US011155933B2

(12) United States Patent
Delaney, Jr. et al.

(10) Patent No.: US 11,155,933 B2
(45) Date of Patent: Oct. 26, 2021

(54) LUBRICIOUS, BIOCOMPATIBLE HYDROPHILIC THERMOSET COATING USING INTERPENETRATING HYDROGEL NETWORKS

(71) Applicant: Cardiac Pacemakers, Inc., St. Paul, MN (US)

(72) Inventors: Joseph T. Delaney, Jr., Minneapolis, MN (US); Jeannette C. Polkinghorne, Spring Lake Park, MN (US); Adegbola O. Adenusi, Burnsville, MN (US); David R. Wulfman, Minneapolis, MN (US); Kasyap Seethamraju, Eden Prairie, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 231 days.

(21) Appl. No.: 16/233,544

(22) Filed: Dec. 27, 2018

(65) Prior Publication Data
US 2019/0127886 A1    May 2, 2019

Related U.S. Application Data

(62) Division of application No. 14/329,123, filed on Jul. 11, 2014, now abandoned.
(Continued)

(51) Int. Cl.
*A61N 1/05* (2006.01)
*D01D 5/00* (2006.01)

(52) U.S. Cl.
CPC ............. *D01D 5/0023* (2013.01); *A61N 1/05* (2013.01); *A61N 1/056* (2013.01); *A61N 1/0541* (2013.01);
(Continued)

(58) Field of Classification Search
CPC ........ A61N 1/0541; A61N 1/056; A61N 1/05; A61N 1/0534; A61N 1/0543;
(Continued)

(56) References Cited

U.S. PATENT DOCUMENTS 4,281,668 A * 8/1981 Richter .................... A61N 1/05
                                                  607/121
5,157,929 A   10/1992 Hotaling
(Continued)

FOREIGN PATENT DOCUMENTS

AU    2012295332 B2   2/2014
CN     101636187 A    1/2010
(Continued)

OTHER PUBLICATIONS

Datta, Jhunu and Nandi, Arun K. "Cocrystallization of Poly(Vinylidene Fluroide) and Vinylidene Fluoride-Tetrafluoro-ethylene Copolymer Blends: 3. Structural Study." Polymer 38(11):2719-2724, 1997.
(Continued)

*Primary Examiner* — Jason L Vaughan
*Assistant Examiner* — Amanda Kreiling
(74) *Attorney, Agent, or Firm* — Faegre Drinker Biddle & Reath LLP (57) ABSTRACT

A medical electrical lead includes an insulative lead body extending from a distal region to a proximal region and a conductor disposed within the insulative lead body and extending from the proximal region to the distal region. An electrode is disposed on the insulative lead body and is in electrical contact with the conductor. The medical electrical lead also includes a cross-linked hydrophilic polymer coating disposed over at least a portion of the electrode. The cross-linked hydrophilic polymer coating includes a fibrous matrix comprising a plurality of discrete fibers and pores formed between at least a portion of the fibers and a
(Continued)

hydrophilic polyethylene glycol-containing hydrogel network disposed within the pores of the fibrous matrix.

20 Claims, 6 Drawing Sheets

Related U.S. Application Data (60) Provisional application No. 61/856,959, filed on Jul. 22, 2013.

(52) U.S. Cl.
CPC .......... *A61N 1/0534* (2013.01); *A61N 1/0543* (2013.01); *A61N 1/0551* (2013.01); *D01D 5/0007* (2013.01); *Y10T 29/49982* (2015.01)

(58) Field of Classification Search
CPC ............ A61N 1/0551; Y10T 29/49616; Y10T 29/4998; Y10T 29/49982; Y10T 29/53204; Y10T 29/49826; Y10T 29/49885; Y10T 29/49888
See application file for complete search history.

(56) References Cited

U.S. PATENT DOCUMENTS

| | | | |
|---|---|---|---|
| 5,861,023 A * | 1/1999 | Vachon | A61N 1/0563 607/121 |
| 6,120,845 A | 9/2000 | Pease | |
| 7,091,412 B2 | 8/2006 | Wang et al. | |
| 7,689,291 B2 | 3/2010 | Polkinghorne et al. | |
| 7,908,016 B2 | 3/2011 | Atanasoska et al. | |
| 8,070,718 B2 | 12/2011 | Weber et al. | |
| 8,903,506 B2 | 12/2014 | Arnholt et al. | |
| 8,965,531 B2 | 2/2015 | Arnholt et al. | |
| 9,011,754 B2 | 4/2015 | Leong et al. | |
| 9,415,206 B2 | 8/2016 | Arnholt et al. | |
| 9,855,415 B2 | 1/2018 | Delaney, Jr. et al. | |
| 10,465,318 B2 | 11/2019 | Gruba et al. | |
| 2004/0175406 A1 | 9/2004 | Schwarz | |
| 2004/0230271 A1 | 11/2004 | Wang et al. | |
| 2005/0149158 A1 | 7/2005 | Hunter et al. | |
| 2006/0129179 A1 | 6/2006 | Weber et al. | |
| 2006/0159837 A1 | 7/2006 | Kaplan et al. | |
| 2006/0264577 A1 | 11/2006 | Faust et al. | |
| 2007/0051531 A1 | 3/2007 | Borganonkar et al. | |
| 2007/0067882 A1 | 3/2007 | Atanasoska et al. | |
| 2007/0239245 A1 | 10/2007 | Borgaonkar et al. | |
| 2007/0255378 A1 * | 11/2007 | Polkinghorne | D01D 5/0084 607/119 |
| 2008/0071338 A1 * | 3/2008 | Jiang | A61N 1/056 607/119 |
| 2009/0076530 A1 | 3/2009 | Fukutomi et al. | |
| 2009/0099441 A1 | 4/2009 | Giszter et al. | |
| 2009/0099634 A1 | 4/2009 | Atanasoska et al. | |
| 2009/0105796 A1 | 4/2009 | Atanasoska et al. | |
| 2009/0326077 A1 | 12/2009 | Desai et al. | |
| 2010/0023104 A1 | 1/2010 | Desai et al. | |
| 2010/0057197 A1 | 3/2010 | Weber et al. | |
| 2010/0069578 A1 | 3/2010 | Faust et al. | |
| 2010/0093093 A1 | 4/2010 | Leong et al. | |
| 2010/0179298 A1 | 7/2010 | Faust et al. | |
| 2010/0190254 A1 | 7/2010 | Chian et al. | |
| 2010/0241204 A1 | 9/2010 | Scheuermann | |
| 2010/0241208 A1 | 9/2010 | Pinchuk | |
| 2011/0021899 A1 | 1/2011 | Arps et al. | |
| 2011/0054580 A1 | 3/2011 | Desai et al. | |
| 2011/0054581 A1 | 3/2011 | Desai et al. | |
| 2011/0137389 A1 | 6/2011 | Polkinghorne et al. | |
| 2011/0196464 A1 | 8/2011 | Pinchuk | |
| 2013/0013040 A1 | 1/2013 | Desai et al. | |
| 2013/0041442 A1 * | 2/2013 | Arnholt | D01D 5/0023 607/115 |
| 2013/0131765 A1 | 5/2013 | Polkinghorne et al. | |
| 2013/0231733 A1 | 9/2013 | Knisley et al. | |
| 2013/0238086 A1 | 9/2013 | Ballard et al. | |
| 2013/0268062 A1 | 10/2013 | Puckett et al. | |
| 2014/0141152 A1 | 5/2014 | Sostek et al. | |
| 2014/0188212 A1 | 7/2014 | Haselby et al. | |
| 2014/0324141 A1 | 10/2014 | Arnholt et al. | |
| 2015/0025608 A1 | 1/2015 | Delaney et al. | |
| 2015/0064142 A1 | 3/2015 | Green et al. | |
| 2015/0088238 A1 | 3/2015 | Arnholt et al. | |
| 2015/0273110 A1 | 10/2015 | McClellan et al. | |
| 2015/0343200 A1 | 12/2015 | Arnholt et al. | |
| 2017/0021160 A1 | 1/2017 | Delaney et al. | |
| 2018/0179680 A1 | 6/2018 | Gruba et al. | |

FOREIGN PATENT DOCUMENTS

| | | |
|---|---|---|
| CN | 102592973 A | 7/2012 |
| CN | 104383606 A | 3/2015 |
| CN | 105769442 A | 7/2016 |
| EP | 1646486 A2 | 4/2006 |
| GB | 1527592 A | 10/1978 |
| JP | H0411061 A | 1/1992 |
| JP | 2001522654 A | 11/2001 |
| JP | 2004119113 A | 4/2004 |
| JP | 2005523116 A | 8/2005 |
| JP | 2007154336 A | 6/2007 |
| JP | 2008500104 A1 | 1/2008 |
| JP | 2008515611 A | 5/2008 |
| JP | 2008253297 A | 10/2008 |
| JP | 2009000100 A | 1/2009 |
| JP | 2009507577 A | 2/2009 |
| JP | 2009531140 A | 9/2009 |
| JP | 2009535182 A | 10/2009 |
| JP | 2009540873 A | 11/2009 |
| JP | 2010540105 A | 12/2010 |
| JP | 2012047969 A | 3/2012 |
| JP | 2014156599 A | 8/2014 |
| JP | 2014525279 A | 9/2014 |
| JP | 2015017154 A | 1/2015 |
| JP | 2016160307 A | 9/2016 |
| SU | 132800 A | 1/1960 |
| WO | 1990008466 A1 | 8/1990 |
| WO | 2002089909 A1 | 11/2002 |
| WO | 2003045875 A1 | 6/2003 |
| WO | 2003101505 A1 | 12/2003 |
| WO | 2004041529 A1 | 5/2004 |
| WO | 2005032400 A2 | 4/2005 |
| WO | 2005039664 A2 | 5/2005 |
| WO | 2005065578 A2 | 7/2005 |
| WO | 2005079339 A2 | 9/2005 |
| WO | 2006020425 A1 | 2/2006 |
| WO | 2006041767 A2 | 4/2006 |
| WO | 2006123340 A2 | 11/2006 |
| WO | 2007003199 A1 | 1/2007 |
| WO | 2007030722 A1 | 3/2007 |
| WO | 2007109007 A2 | 9/2007 |
| WO | 2007130900 A2 | 11/2007 |
| WO | 2008008266 A2 | 1/2008 |
| WO | 2008021020 A2 | 2/2008 |
| WO | 2008036460 A1 | 3/2008 |
| WO | 2008055038 A2 | 5/2008 |
| WO | 2008060333 A1 | 5/2008 |
| WO | 2008066538 A1 | 6/2008 |
| WO | 2008066914 A1 | 6/2008 |
| WO | 20080066912 A2 | 6/2008 |
| WO | 2009002984 A2 | 12/2008 |
| WO | 2009140381 A1 | 11/2009 |
| WO | 2010053585 A1 | 5/2010 |
| WO | 2010065484 A1 | 6/2010 |
| WO | 2010107967 A1 | 9/2010 |
| WO | 2011017695 A1 | 2/2011 |
| WO | 2011017698 A1 | 2/2011 |
| WO | 2011028873 A2 | 3/2011 |
| WO | 2013025465 A1 | 2/2013 |
| WO | 2013112793 A1 | 8/2013 |
| WO | 2013151778 A1 | 10/2013 |

(56) References Cited

FOREIGN PATENT DOCUMENTS

| WO | 2015134853 A1 | 9/2015 |
|----|---------------|--------|
| WO | 2016025945 A1 | 2/2016 |

OTHER PUBLICATIONS

De Navarro, C. Urbina, et al. Contribucion Al Estudio De Los Factores Que Influyeron En Falla De Tuberias De PVDF. Acta Microscópica, 13(1):55-61, 2004. [English Abstract].

De Navarro, C. Urbina, et al. Relationship Between the Degradation of PVDF and the Presence of Crystalline Phases Alpha and the Mixed. CIASEM 201: 11th Inter American Congress on Microscopy, E.R.R.B.A.A.O. (UAY), Editor 2011, Merida Yucatan, Mexico.

De Obanos, Mercedes Perez, et al. "Corrosion Selective de las Estructuras Cristalinas del PVDF por Hidroxido de Sodio." Revista de la Facultad de Ingenieria de la U.C.V., 16(2):95-103, 2001, [English Abstract].

He, Fuan, et al. Preparation and Characterization of Electrospun Poly(Vinylidene Fluoride)/Poly(Methyl Methacrylate) Membrane. High Performance Polymers, 26(7):817-825, 2014.

Hong, Lingfei; Pan, Tingrui, "Photopatternable Superhydrophobic Nanocomposites for Microfabrication," Journal of Microelectromechanical Systems, vol. 19, No. 2, (Apr. 2010), pp. 246-253.

Huang, Zheng-Ming et al., "A review on polymer nanofibers by electrospinning and their applications in nanocomposites", Composites Science and Technology, No. 66, 2003, pp. 2223-2253.

International Preliminary Report on Patentability issued in PCT/US2016/043580, dated Feb. 8, 2018, 8 pages.

International Preliminary Report on Patentability issued in PCT/US2017/068412, dated Jul. 11, 2019, 7 pages.

International Preliminary Report on Patentability, Chapter II, issued in PCT/US2012/050260, completed Oct. 28, 2013, 16 pages.

International Preliminary Report on Patentability, Chapter II, issued in PCT/US2012/065896, dated Dec. 18, 2013, 8 pages.

International Search Report and Written Opinion issued in PCT/US2012/050260, dated Dec. 7, 2012, 12 pages.

International Search Report and Written Opinion issued in PCT/US2012/065896, dated Feb. 20, 2013, 9 pages.

International Search Report and Written Opinion issued in PCT/US2016/043580, dated Oct. 13, 2016, 11 pages.

International Search Report and Written Opinion issued in PCT/US2017/068412, dated Apr. 18, 2018, 11 pages.

Jinglei Wu et al., "Enhancing cell infiltration of electrospun fibrous scaffolds in tissue regeneration", Bioactive Materials, vol. 1, No. 1, pp. 56-64, Jul. 26, 2016.

Lee, J. L., "Polymer Nanoengineering for Biomedical Applications", Annals of Biomedical Engineering, 34(1), (2006), 75-88.

Liu, Xin, et al. "In Vivo Wound Healing and Antibacterial Performances of Electrospun Nanofibre Membranes." Journal of BioMedical Materials Research A, 94A(2):499-508, Aug. 2010.

Menini, Richard, et al., "Production of superhydrophobic polymer fibers with embedded particles using the electrospinning technique," Society of Chemical Industry, Polym Int 57, pp. 77-84 (2008). DOI: 10.1002/pi.

Ostwald, W. Studien Uber Die Bildung und Umwandlung Fester Korper—1. Abhandlung: Ubersattingung und Uberkaltung. Zietschrift f. physik. Chemie. XXII. Leipzig, Physiko-chemisches Laboratorium, Feb. 1897, pp. 289-330.

Ross, G. J., et al. Surface Modification of Poly(Vinylidene Fluoride) by Alkaline Treatment Part 2. Process Modification by the Use of Phase Transfer Catalysts. Polymer 42:403-413, 2001.

Ross, G. J., et al. Surface Modification of Poly(Vinylidene Fluoride) by Alkaline Treatment: 1. The Degradation Mechanism. Polymer 41:1685-1696, 2000.

Simonet, Marc; et al. "Ultraporous 3D Polymer Meshes by Low-Temperature Electrospinning: Use of Ice Crystals as a Removable Void Template." Polymer Engineering and Science, 2007, pp. 2020-2026.

Su, Ching-luan et al., "A Study of Hydrophobic Electrospun Membrane Applied in Seawater Desalination by Membrane Distillation," Fibers and Polymers (2012), vol. 13, No. 6, pp. 698-702. DOI 10.1007/s12221-012-0698-3.

Wikipedia. "Gel," [Online], Page last modified Jan. 1, 2017, retrieved from the Internet <https://en.wikipedia.org/wiki/Gel>, 7 pages.

Written Opinion of the International Preliminary Examining Authority issued in PCT/US2012/050260, dated Jul. 18, 2013, 7 pages.

Zhou, Tao; Yao, Yongyi; Xiang, Ruili; Wu, Yurong, "Formation and characterization of polytetrafluoroethylene nanofiber membranes for vacuum membrane distillation," Journal of Membrane Science 453 (2014), pp. 402-408. <www.elsevier.com/locate/memsci>.

\* cited by examiner

LUBRICIOUS, BIOCOMPATIBLE HYDROPHILIC THERMOSET COATING USING INTERPENETRATING HYDROGEL NETWORKS

CROSS-REFERENCE TO RELATED APPLICATION

This application is a division of U.S. application Ser. No. 14/329,123, filed Jul. 11, 2014, which claims priority to U.S. Provisional Application 61/856,959, filed Jul. 22, 2013, which is herein incorporated by reference in its entirety.

TECHNICAL FIELD

The present invention relates to medical devices and methods for manufacturing medical devices. More specifically, the invention relates to coated medical electrical leads and to methods for coating medical electrical leads.

BACKGROUND

Cardiac pacing leads are well known and widely employed for carrying pulse stimulation signals to the heart from a battery operated pacemaker, or other pulse generating means, as well as for monitoring electrical activity of the heart from a location outside of the body. Electrical energy is applied to the heart via an electrode to return the heart to normal rhythm. Some factors that affect electrode performance include polarization at the electrode/tissue interface, electrode capacitance, sensing impedance, and voltage threshold. In all of these applications, it is highly desirable to optimize electrical performance characteristics at the electrode/tissue interface.

A recognized performance challenge of materials conventionally used as electrodes includes the difficulty of controlling tissue in-growth while optimizing the lead performance characteristics at the electrode/tissue interface. This challenge may result in a lead having lower than ideal electrical performance characteristics, which may further reduce over time.

SUMMARY

Disclosed herein are various embodiments of coated medical electrical leads and methods for coating medical electrical leads.

In Example 1, a medical electrical lead includes an insulative lead body extending from a distal region to a proximal region and a conductor disposed within the insulative lead body and extending from the proximal region to the distal region. An electrode is disposed on the insulative lead body and in electrical contact with the conductor. A cross-linked hydrophilic polymer coating is disposed over at least a portion of the electrode. The cross-linked hydrophilic polymer coating includes a fibrous matrix comprising a plurality of discrete fibers and pores formed between at least a portion of the fibers and a hydrophilic polyethylene glycol-containing hydrogel network disposed within the pores of the fibrous matrix.

In Example 2, the medical electrical lead according to Example 1, wherein the fibers of the fibrous matrix include a fluoropolymer.

In Example 3, the medical electrical lead according to Example 1 or 2, wherein the fibers of the fibrous matrix include a poly(vinylidene fluoride-co-hexafluoropropene) (PVDF HFP) polymer.

In Example 4, the medical electrical lead according to any of Examples 1-3, wherein the fibers of the fibrous matrix include a poly(styrene-isobutylene-styrene) (SIBS) tri-block polymer.

In Example 5, the medical electrical lead according to any of Examples 1-4, wherein the fibers of the fibrous matrix include a polycarbonate, polyether, polyester or a polyisobutylene (PIB) polymer.

In Example 6, the medical electrical lead according to any of Examples 1-5, wherein the fibrous matrix is a nonwoven fibrous matrix.

In Example 7, the medical electrical lead according to any of Examples 1-6, wherein the fibrous matrix is an electrospun fibrous matrix.

In Example 8, the medical electrical lead according to any of Examples 1-7, wherein the hydrophilic polyethylene glycol-containing hydrogel includes a polyethylene glycol (PEG) having a number molecular weight (MN) range of about 400 g/mol to about 5,000 g/mol.

In Example 9, the medical electrical lead according to any of Examples 1-8, wherein the hydrophilic polyethylene glycol-containing hydrogel includes a polyethylene glycol (PEG) having a number molecular weight (MN) range of about 5,000 g/mol to about 30,000 g/mol.

In Example 10, the medical electrical lead according to any of Examples 1-9, wherein the hydrophilic polyethylene glycol-containing hydrogel network is disposed within at least a portion of the pores of the fibrous matrix. The pores form a network that extends from a first surface of the fibrous matrix to a second surface of the fibrous matrix which is opposite the first surface.

In Example 11, a medical electrical lead includes an insulative lead body extending from a distal region to a proximal region and a conductor disposed within the insulative lead body and extending from the proximal region to the distal region. An electrode is disposed on the insulative lead body and in electrical contact with the conductor. A cross-linked hydrophilic polymer coating is disposed over at least a portion of the lead body. The cross-linked hydrophilic polymer coating includes a fibrous matrix comprising a plurality of discrete fibers and pores formed between at least a portion of the fibers and a hydrophilic polyethylene glycol-containing hydrogel network disposed within the pores of the fibrous matrix.

In Example 12, a method of forming a cross-linked hydrophilic coating on an implantable medical electrical lead having an insulative lead body and an electrode disposed on the insulative lead body. The method includes disposing within at least a portion of pores of the a nonwoven fibrous matrix a hydrogel comprising at least one polyethylene glycol containing polymer, such that the hydrogel continuously extends from a first surface to an opposite second surface of the nonwoven fibrous matrix. The method also includes curing the hydrogel to the nonwoven fibrous matrix to form the cross-linked hydrophilic coating.

In Example 13, the medical electrical lead according to Example 12, wherein the hydrogel is cured using one of a thermoinitiator and a photoinitiator curing initiator.

In Example 14, the medical electrical lead according to Example 12 or 13, wherein the hydrogel is cured using benzoyl peroxide.

In Example 15, the medical electrical lead according to any of Examples 12-14, further including forming the nonwoven fibrous matrix by using one of an electrospinning process and a melt blowing process.

In Example 16, the medical electrical lead according to any of Examples 12-15, further including plasma treating the nonwoven fibrous matrix prior to applying the hydrogel to the nonwoven fibrous matrix.

In Example 17, the medical electrical lead according to any of Examples 12-16, further includes disposing the hydrogel within at least a portion of the pores by one of dip coating, roll coating, spray coating, drop coating, and flow coating.

In Example 18, the medical electrical lead according to any of the Examples 12-17, further includes disposing the cross-linked hydrophilic coating onto the electrode.

In Example 19, the medical electrical lead according to any of the Examples 12-18, further includes disposing the cross-linked hydrophilic coating onto the electrode before the electrode is assembled onto the implantable medical electrical lead.

In Example 20, the medical electrical lead according to any of the Examples 12-19, further includes disposing within at least a portion of pores of a nonwoven fibrous matrix the hydrogel such that the hydrogel covers at least a portion of the surfaces of fibers of the nonwoven fibrous matrix.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
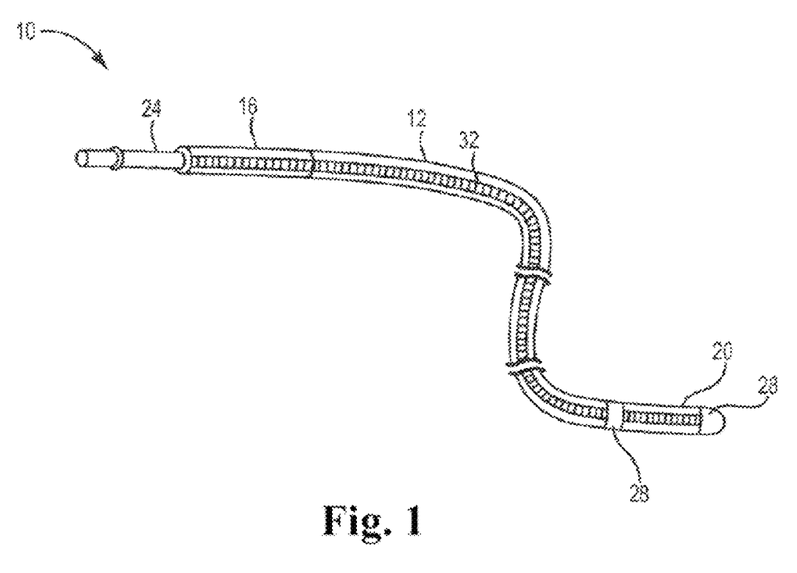
FIG. 1 is a schematic view of a medical electrical lead according to embodiments of the present invention.

FIG. 1 is a partial cross-sectional view of a medical electrical lead 10, according to various embodiments of the present disclosure. According to some embodiments, the medical electrical lead 10 can be configured for implantation within a patient's heart. According to other embodiments, the medical electrical lead 10 is configured for implantation within a patient's neurovascular regions. In yet another embodiment, the lead 10 can be a lead 10 for a cochlear implant. Thus, the electrical lead 10 can be used for a wide range of medical applications that deliver an electrical shock or pulse.

The medical electrical lead 10 includes an elongated, insulative lead body 12 extending from a proximal end 16 to a distal end 20. The proximal end 16 is configured to be operatively connected to a pulse generator (not shown) via a connector 24. At least one conductor 32 extends from the connector 24 at the proximal end 16 of the lead 10 to one or more electrodes 28 at the distal end 20 of the lead 10. The conductor 32 can be a coiled or cable conductor. According to some embodiments where multiple conductors 32 are employed, the lead 10 can include a combination of coiled and cable conductors 32. When a coiled conductor 32 is employed, according to some embodiments, the conductor 32 can have either a co-radial or a co-axial configuration.

The lead body 12 is flexible, but substantially non-compressible along its length, and has a suitable cross-sectional shape. For example, lead body 12 may have a generally circular cross-sectional shape. The lead body 12 may be of a suitable size for implantation. For example, an outer diameter of the lead body 12 may range from about 2 to about 15 French. The lead body 12 may include a suitable bio-compatible, electrically insulative material. For example, in some embodiments, the lead body 12 may include silicone or polyurethane. In some embodiments, the lead body 12 may have a substantially uniform composition along its length. In other embodiments, the composition of the lead body 12 may vary in any direction, including along the length and/or thickness.

The medical electrical lead 10 can be unipolar, bipolar, or multi-polar depending upon the type of therapy to be delivered. In some embodiments of the present disclosure employing multiple electrodes 28 and multiple conductors 32, each conductor 32 is adapted to be connected to an individual electrode 28 in a one-to-one manner allowing each electrode 28 to be individually addressable. Additionally, the lead body 12 can include one or more lumens adapted to receive a guiding element such as a guidewire or a stylet for delivery of the lead 10 to a target location within a patient's heart.

The electrodes 28 can have any electrode 28 configuration as is known in the art. According to one embodiment of the present disclosure, at least one electrode 28 can be a ring or partial ring electrode 28. According to another embodiment, at least one electrode 28 is a shocking coil. According to yet another embodiment of the present disclosure, at least one electrode 28 includes an exposed electrode 28 portion and an insulated electrode 28 portion. In some embodiments, a combination of electrode 28 configurations can be used. The electrodes 28 can be coated with or formed from platinum, stainless steel, titanium, tantalum, palladium, MP35N, other similar conductive material, alloys of any of the foregoing including platinum-iridium alloys, and other combinations of the foregoing including clad metal layers or multiple metal materials.

According to various embodiments, the lead body 12 can include one or more fixation members (not shown) for securing and stabilizing the lead body 12 including the one or more electrodes 28 at a target site within a patient's body. The fixation member(s) can be active or passive. An exemplary active fixation member includes a screw-in fixation member. Examples of passive fixation members can include pre-formed distal portions of the lead body 12 adapted to bear against vessel walls and/or expandable tines provided at the distal end 20 of the lead body 12.

Figure 2A:
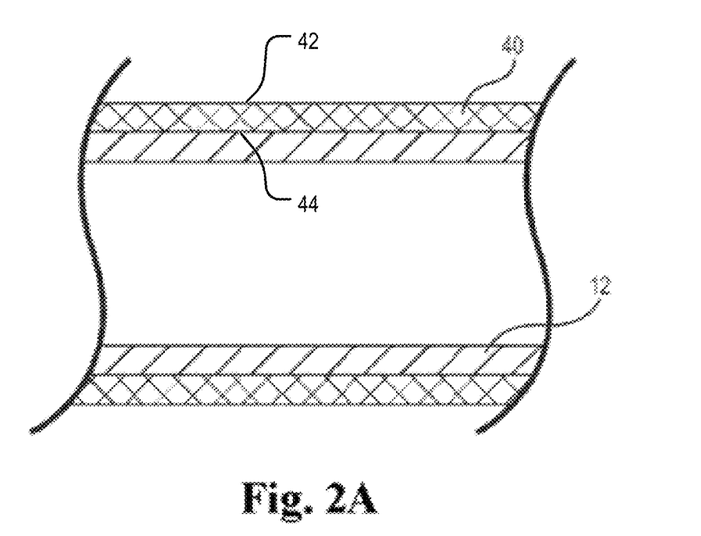
FIGS. 2A and 2B are schematic longitudinal cross-sections of a medical electrical lead according to embodiments of the present invention.
Figure 2B:
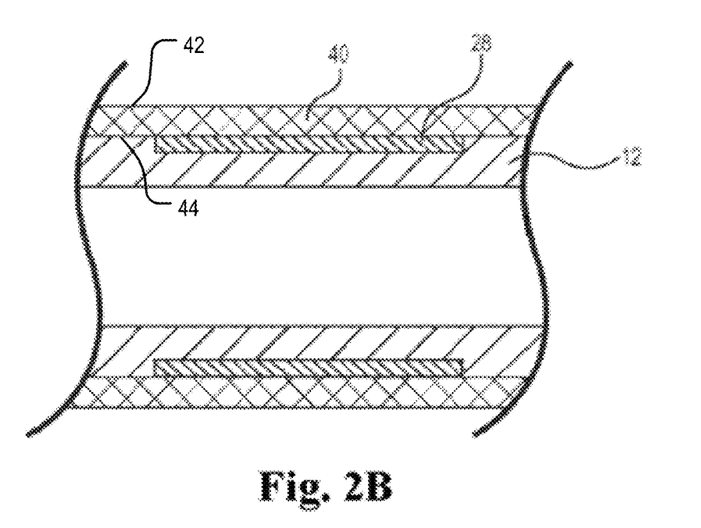

The lead 10 includes a cross-linked hydrophilic polymer coating 40 that is disposed over various parts of the insulative lead body 12. FIGS. 2A and 2B are schematic longitudinal cross-sectional views of the lead 10 of FIG. 1, in which internal structure has been removed for clarity, and provide illustrative but non-limiting examples of regions of the lead 10 that may include a cross-linked hydrophilic polymer coating 40.

FIG. 2A shows the cross-linked hydrophilic polymer coating 40 disposed over at least a portion of the insulative lead body 12. The cross-linked hydrophilic polymer coating 40 includes a first surface 42 and a second opposite surface 44. The illustrated portion of the insulative lead body 12 may be adjacent an electrode 28, or it may be spaced apart from the electrode 28.

In contrast, FIG. 2B illustrates the cross-linked hydrophilic polymer coating 40 disposed over the electrode 28. While the cross-linked hydrophilic polymer coating 40 is illustrated as entirely covering the electrode 28, in some embodiments the cross-linked hydrophilic polymer coating 40 may cover only a portion of the electrode 28. For example, the cross-linked hydrophilic polymer coating 40 may cover a majority or a minority portion of the electrode 28. In some embodiments, the coating 40 may cover any portion of the electrode 28, such as at least one of the ends or at least one of the intermediate portions of the electrode 28.

The cross-linked hydrophilic polymer coating 40 may be of any suitable thickness that delivers electrophysiological therapy through the polymer coating 40. For example, the cross-linked hydrophilic polymer coating 40 may have a thickness in the range of about 500 nanometer (nm) to 300 microns. A suitable coating thickness range also includes the range of about 15 microns to 250 microns, for example. In other examples, the average coating thickness of the cross-linked hydrophilic polymer coating 40 may be about 90 microns (or 0.0035 inches).

In some embodiments, the cross-linked hydrophilic polymer coating 40 may be formed directly on a portion of the lead 10, such as the lead body 12, for example, after the lead 10 is assembled. Alternatively, the cross-linked hydrophilic polymer coating 40 may be formed directly on a component of the lead 10, such as on the electrode 28, for example, before the lead 10 is assembled. In some embodiments, the cross-linked hydrophilic polymer coating 40 may be formed separately on a substrate and then subsequently disposed onto a portion of the lead 10, either before or after assembly of the lead 10. For example, the cross-linked hydrophilic coating 40 may be formed on a substrate as a thin film and then subsequently transferred from the substrate to be disposed on a portion of the lead 10 during the lead assembly.

The cross-linked hydrophilic polymer coating 40 may provide one or more beneficial functionalities to the lead 10. In some embodiments, the cross-linked hydrophilic polymer coating 40 may improve the electrical conductivity of the lead 10. In certain embodiments, the cross-linked hydrophilic polymer coating 40 may increase the impedance of the lead 10. In other embodiments, the cross-linked hydrophilic polymer coating 40 may minimize cellular in-growth and prevent tissue attachment to the lead 10. In yet other embodiments, the cross-linked hydrophilic polymer coating 40 may provide a bio-stable surface for a least a portion of the lead 10.

Figure 3:
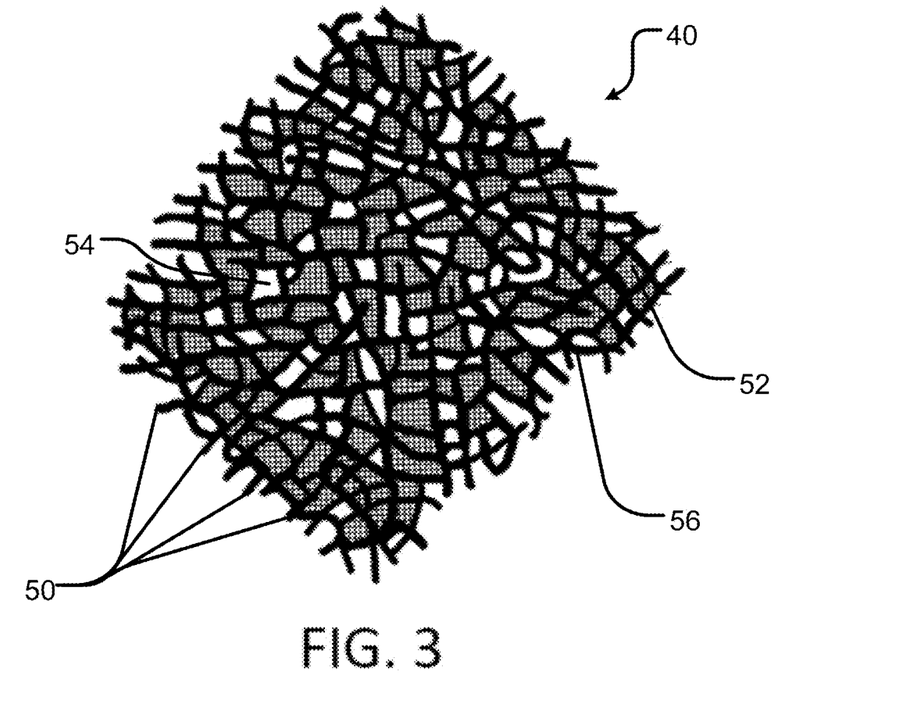
FIG. 3 is a schematic illustration of a cross-linked hydrophilic polymer coating.

FIG. 3 shows an illustrative, but non-limiting example of a cross-linked hydrophilic polymer coating 40 including a fibrous matrix 50 and a hydrophilic hydrogel 52. The fibrous matrix 50 is a structure comprising a plurality of discrete fibers 56. As shown in FIG. 3, the hydrogel 52 is a network of hydrophilic polymer chains located between the fibers 56 of the fibrous matrix 50. Hydrophilicity (also termed as wettability) characterizes the ability of a surface to absorb a liquid, such as water. In contrast, hydrophobicity characterizes an inability of a surface to absorb a liquid, otherwise described as the ability of a surface to repel a liquid, such as water.

The fibrous matrix 50 includes fibers 56 that overlap with one another to create pores 54, or spaces, between a given fiber 56 and one or more neighboring fibers 56. The pores 54 may be formed between neighboring fibers 56 in any direction, including along the length, width and thickness of the fibrous matrix 50. The pores 54 of the fibrous matrix 50 may vary in shape and size. The pores 54 may be interconnected with other pores 54 within the matrix 50. In some embodiments, the pores 54 create a continuous porous network within the matrix 50. In some embodiments, the pores 54 create a continuous porous network from the first surface 42 of the fibrous matrix 50 to the second opposite surface 44 of the fibrous matrix 50 (see FIGS. 2A and 2B). In certain embodiments, the plurality of pores 54 created by the fibers 56 may extend through the matrix 50 in all three spatial directions (i.e., in the x, y, z directions).

In some embodiments, as shown in FIG. 3, the fibrous matrix 50 may be a nonwoven matrix. For example, the fibrous matrix 50 may comprise a plurality of randomly aligned fibers 56 in certain embodiments. As further described herein, a randomly aligned fibrous matrix 50 may be formed by various methods that include, for example, blow melting and electrospinning. In other embodiments, the fibrous matrix 50 may be a woven matrix in which the fibers 56 are oriented in a repeating pattern or configuration.

The fibers 56 of the fibrous matrix 50 may have diameters in the range of about 100 nanometer (nm) to 10,000 nm, for example. The fiber diameter size may be about 100 nm to 3,000 nm, for example. Suitable fiber diameter sizes also include about 40 nm to 2,000 nm, about 100 nm to 1,500 nm or about 100 nm to 1,000 nm, for example. In still further examples, the fiber diameter may be 100 nm to 800 nm, or 100 nm to 400 nm. In other examples, the average fiber diameter may be 400 nm to 10 microns or 800 nm to 10 microns.

As mentioned previously herein, the fibers 56 within the fibrous matrix 50 can create pores 54 of varying sizes within the matrix 50. Fiber configuration and diameter may affect average pore size and range of the pore size of the pores 54 within the matrix 50. For example, a nonwoven fibrous matrix 50 having fibers 56 with a diameter ranging between 0.2-1.0 microns may produce a matrix 50 having a pore size range between 1 nm and 0.5 microns.

Suitable materials for the fibers 56 of the fibrous matrix 50 include both conductive and non-conductive polymer materials. In some embodiments, the fibers 56 of the fibrous matrix 50 are formed from a fluoropolymer material. Suitable fluoropolymer materials for the fibers 56 may include polyvinylidene fluoride (PVDF) and poly(vinylidene fluoride-co-hexafluoropropene) (PVDF-HFP). Other examples of suitable polymer materials for the fibers 56 include, and are not limited to, polyurethane, polycarbonate, polyether, polyester, polyisobutylene (PIB) polyurethane, polyamide, nylon 6, nylon 12, and polyetherimide. In some embodiments, the fibers 56 of the fibrous matrix 50 are formed from a poly(styrene-isobutylene-styrene) (SIBS) tri-block polymer.

The hydrogel 52 is located in between the fibers 56, i.e. within the pores 54, of the fibrous matrix 50. In some embodiments, the hydrogel 52 is disposed within the pores 54 of the fibrous matrix 50 such that at least a portion of the surfaces of individual fibers 56 within the matrix 50 are covered by the hydrogel 52. In certain embodiments, the hydrogel 52 may be disposed within the pores 54 to cover a substantial portion or a majority portion of the fibers 56 within the matrix 50. In other embodiments, the hydrogel 52 may be disposed within the pores 54 to cover only a minority portion of the fibers 56 within the matrix 50. In some embodiments, the hydrogel 52 may be disposed within at least a portion of the pores 54 of the matrix 50.

In some embodiments, when the hydrogel 52 is disposed within the pores 54, the hydrogel 52 may either completely fill or partially fill the pores 54 of the fibrous matrix 50. For example, the hydrogel 52 may fill at least one-third of the total volume of the pores 54 within the fibrous matrix 50. In another example, the hydrogel 52 may fill at least three-fourths of the total volume of the pores 54 within the fibrous matrix 50. In some embodiments, the hydrophilic hydrogel 52 may interpenetrate the pores 54 of the fibrous matrix 50 and create an interconnected hydrogel network throughout the interior of the fibrous matrix 50. In some embodiments, the hydrogel network may extend from a first surface 42 of the cross-linked hydrophilic polymer coating 40 to a second and opposite surface 44 of the polymer coating 40 by interpenetrating, filling, or being disposed within the pores of the matrix 50. The hydrogel 52 serves to increase the hydrophilicity of the fibrous matrix 50, which in turn, may provide the lead 10 with increased sensing and pacing properties.

Suitable materials for the hydrogel 52 include materials that increase the hydrophilicity of the cross-linked hydrophilic polymer coating 40 as compared to the fibrous matrix 50. In some embodiments, the hydrogel 52 may comprise one or more thermoset polymers. In other embodiments, the hydrogel 52 may comprise one or more thermoplastic polymers. In yet other embodiments, the hydrogel may comprise a combination of thermoplastic and thermoset polymers. In some embodiments, the hydrogel 52 comprises a polyethylene glycol (PEG) or a PEG derivative, for example, chitosan-PEG, thiol-PEG, maleimide-PEG, amino-PEG, azide-PEG, and carboxyl-PEG. Examples of other hydrophilic materials include, but are not limited to, poly [N-(2-hydroxypropyl) methacrylamide] (PHPMA), poly(vinyl pyrrolidone), polyethylene/oligoethylene, polyHEMA, polytetraglyme, hyalorunic acid, chitosan, and any derivatives thereof.

The average number molecular weight of the hydrogel polymer constituent may affect the physical integrity of the cross-linked hydrophilic polymer coating 40. For example, a hydrogel 52 comprising a low number molecular weight PEG may yield a more ductile polymer coating 40 than one that uses a hydrogel 52 comprising a high number molecular weight PEG. In some embodiments, a hydrogel 52 comprises a polymer having a low number molecular weight. For example, a low number molecular weight (MN) PEG may have a number molecular weight range from about 400 g/mol to 5,000 g/mol. In other embodiments, a hydrogel 52 comprises a polymer having a high number molecular weight. For example, a high number molecular weight PEG may have a number molecular weight range from about 5,000 g/mol to 30,000 g/mol. In some examples, a suitable number molecular weight for PEG may range from about 550 g/mol to 1,000 g/mol.

In some embodiments, the hydrogel 52 may be produced by cross-linking a hydrogel solution that also includes a curing initiator. Cross-linking may be achieved using a wide variety of free radical initiators, such as a thermal initiator or a photoinitiator. A thermal initiator is a chemical compound that decomposes and produces free radicals when subjected to heat. A photoinitiator is a chemical compound that produces free radicals when exposed to UV light. The curing initiator may be added to the hydrogel solution prior to the hydrogel 52 being applied to the fibrous matrix 50.

In some embodiments, peroxide may be used as the free radical initiator. Peroxide free radical initiators are thermal initiators that may be prepared from alcohols, ketones, and acids. Such peroxides may also be further stabilized or derivatized through the formation of ethers, acetals, and esters. Examples of commonly commercially available peroxides include, but are not limited to, benzoyl peroxide, 2-butanone peroxide, t-butylperacetate, t-butylperoxide, 2,5-di(t-butylperoxy)-2,5-dimethyl-3-hexyne, dicumyl peroxide, 2,4-pentanedione peroxide, 1,1-bis(tert-butylperoxy)cyclohexane, lauroyl peroxide, t-butylperoxy 2-ethylhexyl carbonate.

In other embodiments, an azo initiator may be used as the free radical initiator to cross-link hydrophilic hydrogels 52. Azo initiators are thermal initiators derived from diasene and have the functional group R—N+N—R', where R and R' are either an aryl or alkyl group. Examples of azo free radical initiators include, but are not limited to, 2,2'-azobisisobutyronitrile (AIBN), 1,1'-azobis(cyclohexanecarbonitrile), and 4,4-azobis(4-cyanovaleric acid).

In some embodiments, a photoinitiator may be used as the free radical initiator. Examples of free radical photoinitiators include, but are not limited to, 4-(2-hydroxyethoxy)phenyl-(2-hydroxy-2-propyl)ketone (such as Irgacure® 2959, available from BASF), benzil, benzoin, benzophenone, 2,2-dimethoxy-2-phenylacetophenone, acetophenone-based derivatives, and benzyl-based derivatives.

The hydrophilicity characteristics of the hydrogel 52, the fibrous matrix 50, and/or the cross-linked hydrophilic polymer coating 40 may be determined using a wettability test, for example, the AATCC Test Method 39-1977 promulgated by the American Association of Textile Chemists and Colorists for the evaluation of wettability of fabric. Hydrophilicity characteristics may also be assessed using, for example, the ASTM Test Method D5725-99 promulgated by the American Society for Testing and Materials, which assesses the surface wettability and absorbency of sheeted materials using an automated contact angle tester. Typically, the wettability test records the average time of a liquid droplet to visibly wet, or to be absorbed by, a tested material.

Figure 4:
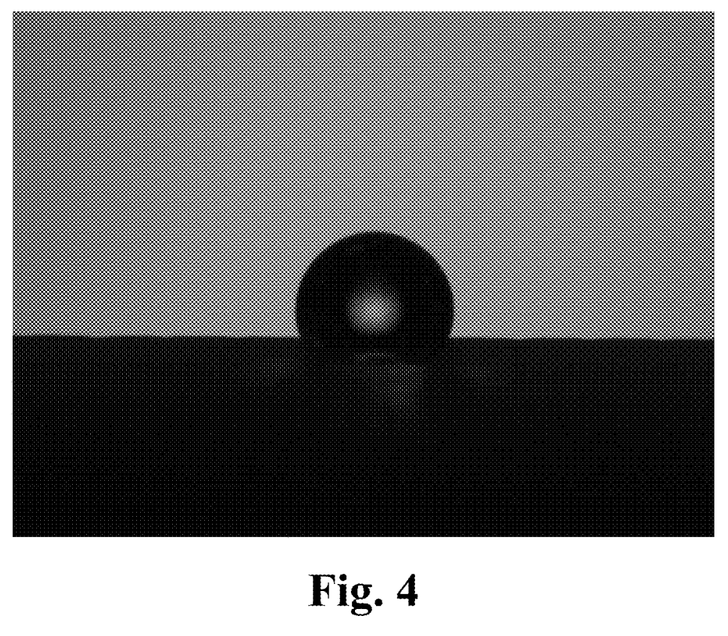
FIG. 4 is an image of a water droplet on the surface of an exemplary uncoated fibrous matrix.
Figure 5:
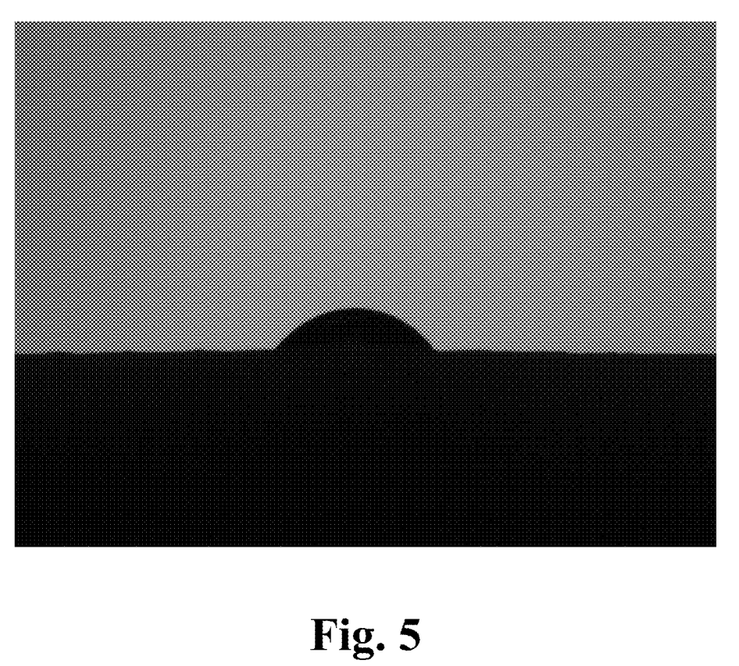
FIG. 5 is an image of a water droplet on the surface of an exemplary cross-linked hydrophilic polymer coating.

The hydrophilicity (or wettability) characteristics of a material may also be determined using a contact angle test. Contact angle test measurements assess the wettability characteristics of a material by observing the spreading of a given liquid over a given surface. For example, a bead of liquid will form absent complete wetting. In the contact angle test, a liquid droplet is placed on a solid surface and is surrounded by a gas. The contact angle ($\theta_c$) is the angle formed by the liquid droplet at the three phase boundary, or a liquid, gas, and solid intersection point. A liquid droplet on a hydrophobic surface will exhibit a high contact angle (see FIG. 4) while a liquid droplet on a hydrophilic surface will exhibit a smaller contact angle (see FIG. 5), or no contact angle if the droplet has been completely absorbed into the solid surface. Generally, the contact angle for a hydrophobic surface is less than 90 degrees while the contact angle for a hydrophilic surface is greater than 90 degrees.

Hydrogels 52 may be applied to the fibrous matrix 50 to create a cross-linked hydrophilic polymer coating 40 that is more hydrophilic than the fibrous matrix 50. The hydrophilicity of a material composed of a fibrous matrix 50 may therefore be enhanced by disposing the hydrogel 52 within the pores 54 of the fibrous matrix 50. In some embodiments, the hydrogel 52 is disposed within the pores 54 of a fibrous matrix 50 having fibers 56 that exhibit a lower hydrophilicity than the hydrogel 52. For example, a PEG hydrogel 52 may be disposed within the pores 54 of a SIBS fibrous matrix 50 to produce a polymer coating 40 that is more hydrophilic than the matrix 50 because the PEG hydrogel 52 is a more hydrophilic material than the SIBS material. In other embodiments, the hydrogel 52 is disposed within the pores 54 of a fibrous matrix 50 having fibers 56 that exhibit hydrophobicity.

I. Method of Creating a Cross-Linked Hydrophilic Coating

The cross-linked hydrophilic polymer coating 40 may be constructed using various methods and processes. Non-limiting examples of various methods and processes are provided hereinafter.

The fibrous matrix 50 may be constructed using various processes, for example, electrospinning and/or melt blowing. The processes discussed herein or other similar processes may be used to construct a fibrous matrix 50. In certain embodiments, the fiber matrix 50 may be formed partially or completely with fibers 56 using modified electrospinning and melt-blowing techniques. Methods for forming the fibrous matrix 50 are generally described in U.S. application Ser. No. 13/571,553, filed Aug. 10, 2012, entitled METHOD FOR COATING DEVICES USING ELECTROSPINNING AND MELT BLOWING, which is incorporated herein by reference in its entirety.

In melt-blowing, an apparatus is configured to accommodate a polymer melt. The polymer melt passes through an orifice and is carried through the orifice via streams of hot air that pass through the apparatus. As the polymer melt exits the orifice, it is met with streams of heated air that helps elongate the polymer melt. As a result, the polymer melt forms fibers 56 that impinge onto a collector. An element to be coated, such as a substrate, may simply be placed on or in front of the collector.

In electrospinning, an electric field may be used to draw a polymer solution or melt from a capillary source. In some embodiments, the capillary source may be a syringe. The polymer solution or melt is drawn to a grounded collector. A high voltage power supply may be used to power the process. The element to be coated, such as a substrate, may be placed on the collector to be coated. Upon drying, the electrospun material may form a thin polymeric web. In some embodiments, the fiber sizes may be controlled by adjusting the relative concentration of polymer in the polymer solution or melt.

The fibrous matrix 50 may undergo surface processing prior to a hydrogel coating application. In some embodiments, the surface processing may change the surface characteristic of the fibrous matrix 50 to facilitate the hydrogel coating application process. In certain embodiments, surface processing may clean the surface, activate the surface, neutralize surface static, and/or realign fiber orientation in the fibrous matrix 50. One example of surface processing includes, but is not limited to, plasma treating.

Plasma treating is a surface modification process that uses ionized gas molecules to alter the surface characteristics of a polymer. Plasma treatment may remove volatile organic compounds from a polymeric material. Also, plasma treatment may be used to activate the surface of a polymeric material that does not typically bond easily, or exhibits hydrophobic characteristics. In some embodiments, plasma treating may be used to temporary activate the surface of the fibrous matrix 50 before the hydrogel 52 is applied.

The hydrogel 52 may be incorporated into the fibrous matrix 50 by producing a hydrogel solution and applying the hydrogel solution onto the matrix 50. For example, PEG may be dissolved in isopropyl alcohol (IPA) to produce a 1.5 wt % to 5 wt % solution. In some embodiments, a centrifugal force mixer, or other similar equipment, may be used to mix the solution.

The hydrogel solution may also include a curing initiator. The curing initiator is a free radical initiator that may be activated later in the process to cross-link the hydrophilic hydrogel 52. The curing initiator may be activated after the hydrogel 52 has been disposed within the pores 54 of the fibrous matrix 50. Once activated, the curing initiator cross-links individual hydrophilic hydrogel chains together.

The hydrogel solution may be applied to the fibrous matrix 50 using various application methods. Examples of possible application methods include, but are not limited to, dip coating, roll coating, spray coating, flow coating, electrostatic spraying, plasma spraying, spin coating, curtain coating and silkscreen coating.

The hydrogel 52 may be subjected to a curing process to crosslink individual hydrogel polymer chains together. The curing process may depend on the curing initiator. In some embodiments, the hydrogel curing process may be initiated by heat or UV light. In other embodiments, vacuum pressure may be used to initiate the free radical initiator and/or to optimize the hydrogel cross-linking process. In some embodiments, the coated fibrous matrix 50 may be placed into an oven to initiate or accelerate the curing of the hydrogel 52. In other embodiments, the hydrogel curing process may be initiated by UV light. Additionally or alternatively, the individual hydrogel polymer chains may crosslink together when the hydrogel contacts an activated surface of the fibrous matrix 50. For example, the surface of the fibrous matrix 50 may be activated by a plasma treatment as described herein, and the hydrogel polymer chains may crosslink together when they contact the activated surface.

As described previously herein, the cross-linked hydrophilic polymer coating 40 may be formed directly on the assembled lead 10 or a component of the lead 10. Alternatively, the polymer coating 40 may be initially formed on a substrate and subsequently transferred onto the lead 10 or a component of the lead 10.

Although the description herein discusses the cross-linked hydrophilic polymer coating 40 on a lead 10, the cross-linked hydrophilic polymer coating 40 may be applied to any medical electrical device such as, but not limited to, implantable electrical stimulation systems and cardiac systems. Examples of implantable electrical stimulation systems include neurostimulation systems, such as spinal cord stimulation (SCS) systems, deep brain stimulation (DBS) systems, peripheral nerve stimulation (PNS) systems, gastric nerve stimulation systems, cochlear implant systems, and retinal implant systems, among others. Examples of cardiac systems include implantable cardiac rhythm management (CRM) systems, implantable cardioverter-defibrillators (ICD's), and cardiac resynchronization and defibrillation (CRDT) devices, among others.

Cross-linked hydrophilic polymer coatings 40 can provide several benefits for medical electric leads 10 and electrodes 28. Cross-linked hydrophilic polymer coatings 40 may be able to improve the wettability of membranes and nanofibrous materials used in medical lead bodies 12 and electrodes 28. As a result, the electrical performance of the electrodes 28 and lead bodies 12 may be significantly improved. Other benefits of the polymer coating 40 may also include providing a biostable surface and preventing cell adhesion to the electrical leads 10 and electrodes 28. In some cases, the cross-linked hydrophilic polymer coating 40 can be a cost-efficient alternative to other alternative hydrophilic structures. Because of the ability of the cross-linked hydrophilic polymer coating 40 to conform to any geometry, the polymer coating 40 may be easily applied to custom electrode geometries. In contrast, alternative hydrophilic structures may be limited to extrusion and molding processes, which cannot accommodate irregular electrode geometries.

Figure 6:
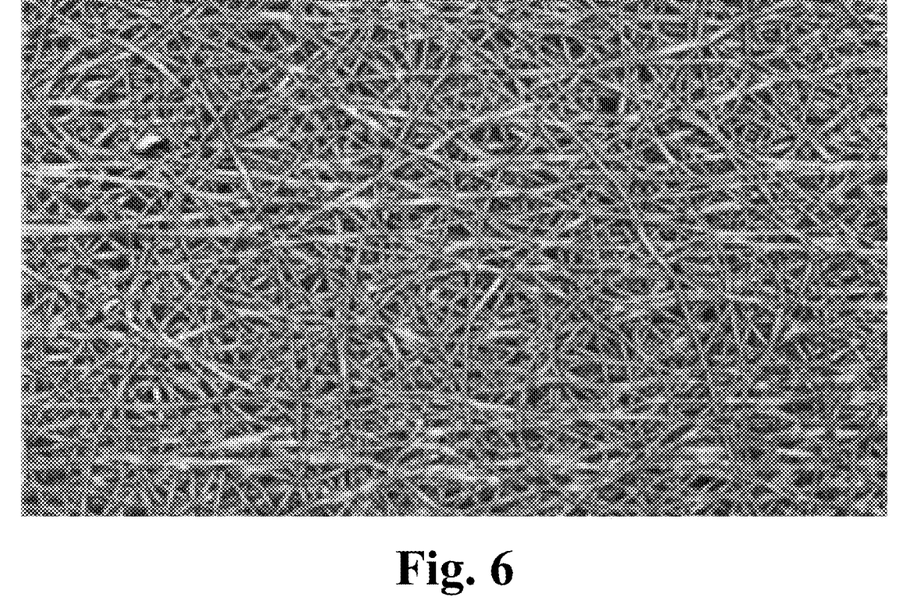
FIG. 6 is a light microscope image of a polyvinylidene fluoride (PVDF) fibrous matrix.
Figure 7:
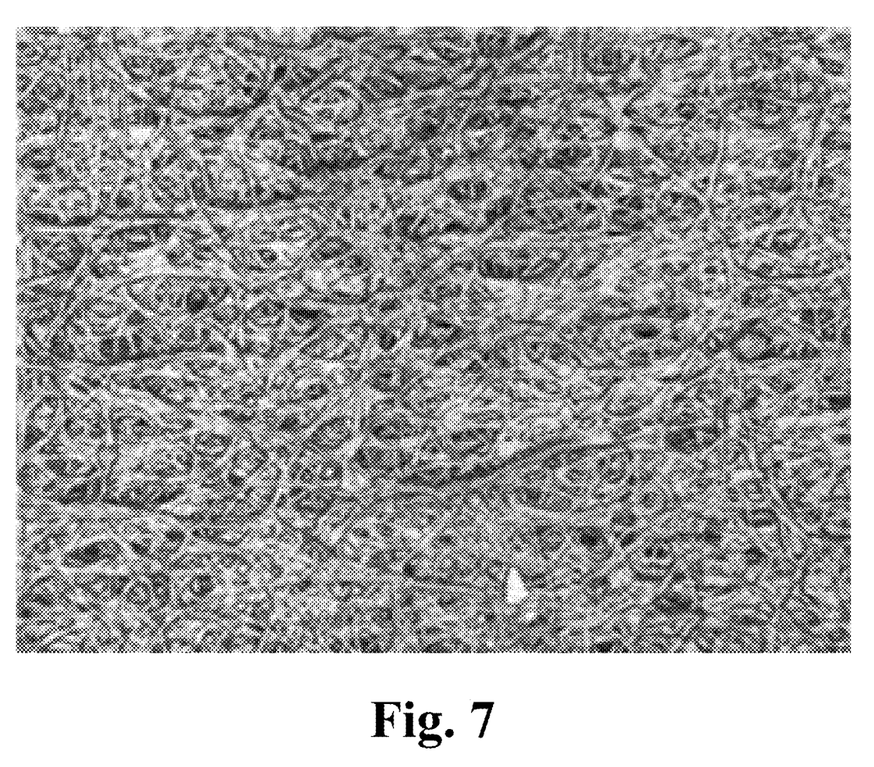
FIG. 7 is a confocal microscope image of a cross-linked hydrophilic polymer coating including a polyethylene glycol (PEG) hydrogel and a PVDF fibrous matrix.

Specific examples of a fibrous matrix 50 and a cross-linked hydrophilic polymer coating 40 are provided herein. FIG. 6 provides an image of a fibrous matrix 50 formed by poly(vinylidene fluoride-co-hexafluoropropene) (PVDF-HFP) fibers 56. FIG. 7 shows an image of a cross-linked hydrophilic polymer coating 40 formed by a polyethylene glycol (PEG) hydrogel 52 and a poly(vinylidene fluoride-co-hexafluoropropene) (PVDF-HFP) fibrous matrix 50. As shown by FIG. 7, the hydrogel 52 is disposed in the spaces, i.e. pores 54, between the fibers 56 and over the surface of the fibers 56 of the fibrous matrix 50.

Example 1

The present invention is more particularly described in the following example, which is intended as illustration only, since numerous modifications and variations within the scope of the present invention will be apparent to those skilled in the art.

Moisture Absorption Comparison Study

Control Samples

Control samples were SIBS matrixes that were constructed using an electrospinning process. Control samples did not contain a hydrogel.

Test Samples

Test samples were cross-linked hydrophilic polymer coating specimens that included a SIBS matrix and a PEG 770 hydrogel. The SIBS matrixes were constructed using an electrospinning process.

The following process steps were used for constructing the cross-linked hydrophilic polymer coating on the test samples.

One gram of polyethylene glycol (PEG) 770 was added to a mixing container, and mixed with 20 mL of isopropyl alcohol (IPA) to obtain a 5% solution of PEG 770 in IPA. The solution of PEG 770 in IPA was thoroughly mixed using a centrifugal force mixer until the PEG 770 had completely dissolved in solution. At least 9 mg of dibenzoyl peroxide was added to the PEG solution and mixed until the dibenzoyl peroxide was completely dissolved in the solution.

The SIBS fibrous matrix was placed in a plasma treatment oven. An argon plasma treatment was applied to clean the surface of the SIBS matrix, followed by an oxygen plasma treatment.

Once the oxygen treatment was completed, the PEG 770/dibenzoyl peroxide mixture was applied to the SIBS matrix 50 by dropping a series of droplets of the hydrogel mixture onto one or more surfaces of the matrix 50.

After application of the mixture, the coated test samples were placed in a vacuum oven at room temperature and vacuum was set to approximately −22 inHg.

Once the target pressure was reached, the oven temperature was increased to 60 degrees Celsius. Samples were subjected to these oven conditions for one hour.

Moisture Absorption Test Method

Test and control samples were each labeled accordingly and placed on one end of a 1.83 mm (or 0.072 inch) diameter rod.

Once each sample was properly placed on a rod, the samples were transferred onto a small faceplate (i.e. polyether ether ketone (PEEK) faceplate).

Prior to testing, samples were subjected to a drying process in a vacuum oven for two hours. The vacuum oven was set to a pressure of −22 inHg and a temperature of 40 degrees Celsius during this drying process.

Once the drying process was completed, the samples were taken out of the vacuum oven and removed from the faceplate. A water droplet was placed on surface of each sample and after three minutes, each sample was observed for water droplet absorption. If the droplet was not visible on the surface of the sample after three minutes, the sample was recorded to have absorbed the water droplet.

Results

TABLE 1

Moisture absorption data

|  | Number of Absorbed Droplet Observations | Total Number of Observations |
| --- | --- | --- |
| Test Samples | 8 | 10 |
| Control Samples | 2 | 10 |

The number of observations of an absorbed droplet in the test group and the control group are shown in Table 1. Observations were made three minutes after the each droplet has been placed on the surface of each sample.

Table 1 shows that the test group had 8 out of 10 observations of an absorbed water droplet. The control group had 2 out of 10 observations of an absorbed water droplet. The results show that a cross-linked hydrophilic polymer coating (i.e. a SIBS fibrous matrix containing a PEG 770 hydrogel) exhibits higher hydrophilicity than a SIBS fibrous matrix containing no hydrogel.

We claim:

1. A method of forming a cross-linked hydrophilic coating on an implantable medical electrical lead having an insulative lead body and an electrode disposed on the insulative lead body, the method comprising:
    disposing within at least a portion of pores of a nonwoven fibrous matrix a hydrogel comprising at least one polyethylene glycol containing polymer, such that the hydrogel continuously extends from a first surface to an opposite second surface of the nonwoven fibrous matrix; and
    curing the hydrogel to the nonwoven fibrous matrix to form the cross-linked hydrophilic coating.

2. The method of claim 1, wherein the hydrogel is cured using one of a thermoinitiator and a photoinitiator curing initiator.

3. The method of claim 2, wherein the hydrogel is cured using benzoyl peroxide.

4. The method of claim 1, further comprising forming the nonwoven fibrous matrix by using one of an electrospinning process and a melt blowing process.

5. The method of claim 1, further comprising plasma treating the nonwoven fibrous matrix prior to applying the hydrogel to the nonwoven fibrous matrix.

6. The method of claim 1, further comprising disposing the hydrogel within at least a portion of the pores by one of dip coating, roll coating, spray coating, drop coating, and flow coating.

7. The method of claim 1, further comprising disposing the cross-linked hydrophilic coating onto the electrode.

8. The method of claim 7, further comprising disposing the cross-linked hydrophilic coating onto the electrode before the electrode is assembled onto the implantable medical electrical lead.

9. The method of claim 1, further disposing within at least a portion of pores of a nonwoven fibrous matrix the hydrogel such that the hydrogel covers at least a portion of the surfaces of fibers of the nonwoven fibrous matrix.

10. A method of forming a cross-linked hydrophilic coating on an implantable medical electrical device, the method comprising:
    applying a hydrogel solution comprising a hydrogel to a nonwoven fibrous matrix disposed over at least a portion of the implantable medical electrical device to dispose the hydrogel within at least a portion of pores of the nonwoven fibrous matrix, such that the hydrogel continuously extends from a first surface to an opposite second surface of the nonwoven fibrous matrix, wherein the hydrogel comprises at least one polyethylene glycol containing polymer; and
    curing the hydrogel to form the cross-linked hydrophilic coating extending from the first surface to the second surface.

11. The method of claim 10, the method further including producing the hydrogel solution and producing the hydrogel solution comprises dissolving the hydrogel in a solvent.

12. The method of claim 11, wherein the solvent includes isopropyl alcohol.

13. The method of claim 11, wherein the hydrogel solution includes from 1.5 wt. % to 5 wt. % of the at least one polyethylene glycol containing polymer.

14. The method of claim 11, wherein the hydrogel solution further comprises a curing initiator selected from the group consisting of a thermoinitiator and a photoinitiator curing initiator.

15. The method of claim 14, wherein the curing initiator comprises benzoyl peroxide.

16. The method of claim 10, further comprising forming the nonwoven fibrous matrix by using one of an electrospinning process and a melt blowing process.

17. The method of claim 16, wherein forming the nonwoven fibrous matrix uses the electrospinning process.

18. The method of claim 10, further comprising plasma treating the nonwoven fibrous matrix prior to applying the hydrogel to the nonwoven fibrous matrix.

19. The method of claim 10, wherein applying the hydrogel solution comprises at least one selected from the group consisting of: dip coating, roll coating, spray coating, drop coating, and flow coating.

20. The method of claim 10, wherein the implantable medical electrical device comprises an insulative lead body and an electrode disposed on the insulative lead body, the nonwoven fibrous matrix disposed onto at least the electrode.

* * * * *